US007201866B2

(12) United States Patent
Stallone

(10) Patent No.: US 7,201,866 B2
(45) Date of Patent: Apr. 10, 2007

(54) CONCRETE TEST CYLINDER MOLD CAP

(76) Inventor: Dominick V. Stallone, 60 Country Rd., Mamaroneck, NY (US) 10543

( * ) Notice: Subject to any disclaimer, the term of this patent is extended or adjusted under 35 U.S.C. 154(b) by 554 days.

(21) Appl. No.: 10/814,699

(22) Filed: Mar. 30, 2004

(65) Prior Publication Data

US 2004/0183233 A1 Sep. 23, 2004

Related U.S. Application Data

(62) Division of application No. 09/923,189, filed on Aug. 6, 2001, now Pat. No. 6,776,387.

(51) Int. Cl.
*B28B 3/00* (2006.01)
*G01N 33/38* (2006.01)

(52) U.S. Cl. ...................................... 264/333; 73/54.03

(58) Field of Classification Search .......... 249/DIG. 4, 249/117; 264/333; 73/54.03, 864.53, 864.59
See application file for complete search history.

(56) References Cited

U.S. PATENT DOCUMENTS

| | | | | | |
|---|---|---|---|---|---|
| 2,644,220 | A | * | 7/1953 | Thaulow | 264/71 |
| 2,697,938 | A | * | 12/1954 | Tanaka | 73/803 |
| 3,974,679 | A | * | 8/1976 | Nasser | 374/51 |
| 4,196,614 | A | * | 4/1980 | McLaughlin | 73/61.41 |
| 4,365,784 | A | * | 12/1982 | De Stasio | 249/139 |
| 4,496,070 | A | * | 1/1985 | Lane, Jr. | 249/117 |
| 4,524,604 | A | * | 6/1985 | Vondran | 73/38 |
| 4,534,225 | A | * | 8/1985 | Peacock et al. | 73/860 |
| 4,615,215 | A | * | 10/1986 | Sugimoto et al. | 73/866 |
| 4,647,690 | A | * | 3/1987 | Drake | 560/245 |
| 4,842,241 | A | * | 6/1989 | Fitzgerald et al. | 249/50 |
| 5,069,417 | A | * | 12/1991 | Boss | 249/74 |
| 5,100,595 | A | * | 3/1992 | Boss | 264/40.1 |
| 5,240,225 | A | * | 8/1993 | Workman et al. | 249/117 |
| 5,257,709 | A | * | 11/1993 | Okabe et al. | 220/62.22 |

FOREIGN PATENT DOCUMENTS

| | | | |
|---|---|---|---|
| DE | 526311 | * | 6/1931 |
| JP | 4361133 | * | 12/1992 |
| JP | 2000-258316 A | * | 9/2000 |

* cited by examiner

*Primary Examiner*—Christina Johnson
*Assistant Examiner*—Patrick Butler
(74) *Attorney, Agent, or Firm*—Holland & Knight LLP

(57) ABSTRACT

A method and apparatus for molding a reproducible uniform concrete test cylinder. Concrete is poured into a concrete test cylinder mold. A cap having at least one excretion hole is placed on the top portion of the concrete test cylinder mold. The cap is pressed against the top portion of the concrete test cylinder mold thereby excreting excess concrete through the excretion hole in the cap. After the cap is separated from the poured concrete, the poured concrete is allowed to cure within the concrete test cylinder mold for a predetermined time. Then, the cured concrete is removed from the concrete test cylinder mold thereby producing a uniform and reproducible concrete test cylinder.

2 Claims, 4 Drawing Sheets

CONCRETE TEST CYLINDER MOLD CAP

CROSS REFERENCES TO RELATED APPLICATIONS

This application claims priority from and is a divisional of commonly owned U.S. Utility patent application Ser. No. 09/923,189, filed Aug. 6, 2001 now U.S. Pat No. 6,776,387, entitled: CONCRETE TEST CYLINDER MOLD CAP, this Utility patent application incorporated by reference herein.

FIELD OF THE INVENTION

This invention relates to concrete testing methods and apparatus and, more particularly, provides a method and apparatus for producing a reproducible concrete test cylinder.

DESCRIPTION OF THE BACKGROUND ART

In the construction of highways, buildings, and other structures utilizing concrete, it is necessary from time to time to test the strength of a sample of the poured concrete to ensure that it has sufficient structural strength required for a particular installation. The most common method of testing concrete has been to take a sample of fresh concrete from a mix at a construction site.

Specifically, fresh concrete is poured into a concrete test cylinder mold to form a cylindrical concrete test cylinder. Upon completion of the cylinder fabrication process, the poured concrete extends above the top of the concrete test cylinder mold. At this point, the concrete that extends above the top of the concrete test cylinder is manually struck off with a trowel or a float. The concrete remaining in the test cylinder mold is then left to set. The following day the concrete test cylinder molds are picked up and delivered to a laboratory where the concrete test cylinders are removed from the concrete test cylinder molds and cured under laboratory conditions.

After curing, the concrete test cylinders are tested for compressive strength. The compressive strength of the concrete test cylinders are a representation of the strength of the concrete placed in the structure.

The problem with the prior art concrete test cylinders that are produced in conventional concrete test cylinder molds is that the concrete test cylinders produced are non-uniform. Specifically, the prior art concrete test cylinder molds produce concrete test cylinders that vary in height, diameter and overall smoothness. The prior art does not ensure that every sample is of the same height, diameter and level. As a result, many concrete test cylinders are non-planar or have a oval diameter at the top of the mold. Accordingly, the accuracy of the test of the concrete test cylinder is reduced since the overall compressive strength of the concrete test cylinder can be erratic due to the non-uniformity of the concrete test cylinder.

Therefore, there exists a need in the art to improve the uniformity of a concrete test cylinder through the use of an efficient and cost effective product.

Nothing in the prior art provides the benefits attendant with the present invention.

Therefore, it is an object of the present invention to provide an improvement which overcomes the inadequacies of the prior art devices and which is a significant contribution to the advancement of the art.

It is therefore an object of the present invention to provide a method and apparatus for reproducibly producing a concrete test sample that is uniform in height, diameter and overall smoothness.

It is a further object of the invention to provide such a sample by a method that is quick and easy to use and also relatively inexpensive when compared to present methods.

Another object of the present invention is to provide a cap that is pressed against the top of a concrete test cylinder mold to excrete excess concrete through at least one excretion hole positioned in the cap.

Yet another object of the present invention is to provide a cap that is rotated against the top of a concrete test cylinder mold to channel excess concrete and air through the use of at least one radial trough positioned in the cap and to excrete the excess concrete and air through at least one excretion hole in the cap.

Still yet another object of the present invention is to provide a cap that is rotated against the top of a concrete test cylinder mold to smooth the surface of the concrete within the concrete test cylinder mold through the use of at least one radial trough positioned in the cap.

Another object of the present invention is to provide a cap that has internal threads for threadedly engaging external threads on a concrete test cylinder mold thereby increasing the rotatability of the cap upon the concrete test cylinder mold.

Yet another object of the present invention is to provide a cap that has a handle for rotating the cap upon the top of a concrete test cylinder mold.

Still yet another object of the present invention is to provide a cap that rotatably separates from concrete after the initial set of the concrete within a concrete test cylinder mold.

Another object of the present invention is to increase the efficiency and simplicity of producing a uniform and reproducible concrete test sample through the placement of a cap with at least one excretion hole onto a concrete test sample mold.

Yet another object of the present invention to provide a method for molding a concrete test cylinder, comprising the steps of pouring concrete into a concrete test cylinder mold, the poured concrete extending above a top portion of the concrete test cylinder mold; placing a cap on the top portion of the concrete test cylinder mold, the cap having at least one excretion hole; pressing the cap against the top portion of the concrete test cylinder mold, whereby excess concrete is excreted through the excretion hole in the cap; rotating the cap prior to initial set of the concrete; curing the poured concrete in the concrete test cylinder mold for a predetermined time; and removing the cured concrete from the concrete test cylinder mold, whereby a reproducible concrete test cylinder is produced.

Still yet another object of the present invention to provide a method for molding a concrete test cylinder, comprising the steps of pouring concrete into a concrete test cylinder mold, the poured concrete extending above a top portion of the concrete test cylinder mold; placing a cap on top of the concrete test cylinder mold, the cap having at least one radial trough and at least one excretion hole; rotating the cap, whereby excess concrete is channeled by the radial trough for excretion though the excretion hole in the cap; rotating the cap prior to initial set of the concrete; curing the poured concrete in the concrete test cylinder mold for a predetermined time; and removing the cured concrete from the concrete test cylinder mold, whereby a reproducible concrete test cylinder is produced.

Another object of the present invention to provide an apparatus for molding a concrete test cylinder, comprising in combination a concrete test cylinder mold having a top portion; and a cap having at least one excretion hole positioned on the top portion of the concrete test cylinder mold, whereby excess concrete is excreted through the excretion hole in the cap.

Yet another object of the present invention to provide an apparatus for molding a concrete test cylinder, comprising in combination a concrete test cylinder mold having a top portion; and a cap having at least one radial trough and at least one excretion hole positioned on the top portion, whereby excess concrete is channeled by the radial trough for excretion though the excretion hole in the cap.

The foregoing has outlined some of the pertinent objects of the present invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises a method and an apparatus for molding a reproducible uniform concrete test sample through the use of a cap having at least one excretion hole.

A feature of the present invention is to provide a method and apparatus for reproducibly producing a concrete test sample that is uniform in height, diameter and overall smoothness.

Another feature of the present invention is to provide such a sample by a method that is quick and easy to use and also relatively inexpensive.

Yet another feature of the present invention is to provide a cap that is pressed against the top of a concrete test cylinder mold to excrete excess concrete through at least one excretion hole positioned in the cap.

Still yet another feature of the present invention is to provide a cap that is rotated against the top of a concrete test cylinder mold to channel excess concrete and trapped air through the use of at least one radial trough positioned in the cap and to excrete the excess concrete and air through at least one excretion hole in the cap.

Another feature of the present invention is to provide a cap that is rotated against the top of a concrete test cylinder mold to smooth the surface of the concrete within the concrete test cylinder mold through the use of at least one radial trough positioned in the cap.

Yet another feature of the present invention is to provide a cap that has internal threads for threadedly engaging external threads on a concrete test cylinder mold thereby increasing the rotatability of the cap upon the concrete test cylinder mold.

Still yet another feature of the present invention is to provide a cap that has a handle for rotating the cap upon the top of a concrete test cylinder mold.

Another feature of the present invention is to provide a cap that rotatably separates from concrete after the initial set of the concrete within a concrete test cylinder mold.

Yet another feature of the present invention is to increase the efficiency and simplicity of producing a uniform and reproducible concrete test sample through the placement of a cap with at least one excretion hole onto a concrete test sample mold.

Still yet another feature of the present invention is to provide a method for molding a concrete test cylinder, comprising the steps of pouring concrete into a concrete test cylinder mold to a point where the poured concrete extends above a top portion of the concrete test cylinder mold. A cap having at least one excretion hole is placed on the top portion of the concrete test cylinder mold. The cap is manually pressed against the top portion of the concrete test cylinder mold thereby forcing excess concrete to be excreted through the excretion hole in the cap. Prior to the initial set of the concrete in the concrete test cylinder mold, the cap is rotated upon the top portion of the concrete test cylinder mold in order to separate the cap from the poured concrete within the concrete test cylinder mold. After the cap is separated from the poured concrete, the poured concrete is allowed to cure within the concrete test cylinder mold for a predetermined time. Then, the cured concrete is removed from the concrete test cylinder mold thereby producing a uniform and reproducible concrete test cylinder.

Another feature of the present invention is to provide a method for molding a concrete test cylinder, comprising the steps of pouring concrete into a concrete test cylinder mold to a point where the poured concrete extends above a top portion of the concrete test cylinder mold. A cap having at least one radial trough and at least one excretion hole is placed on the top portion of the concrete test cylinder mold. The cap is manually pressed and rotated against the top portion of the concrete test cylinder mold thereby channeling excess concrete through the radial troughs for excretion through the excretion hole in the cap. In addition, the radial trough smoothes the surface of the poured concrete within the concrete test cylinder mold. Prior to the initial set of the concrete in the concrete test cylinder mold, the cap is rotated upon the top portion of the concrete test cylinder mold in order to separate the cap from the poured concrete within the concrete test cylinder mold. After the cap is separated from the poured concrete, the poured concrete is allowed to cure within the concrete test cylinder mold for a predetermined time. Then, the cured concrete is removed from the concrete test cylinder mold thereby producing a uniform and reproducible concrete test cylinder.

Yet another feature of the present invention is to provide an apparatus for molding a concrete test cylinder, comprising in combination a concrete test cylinder mold and a cap. The concrete test cylinder mold has a top portion where poured concrete extends therefrom. The cap has at least one excretion hole. The cap is manually positioned on the top portion of the concrete test cylinder mold and then pressed against the top portion of the concrete test cylinder in order to force excess concrete to be excreted through the excretion hole in the cap, thereby creating a uniform concrete test cylinder within the concrete test cylinder mold.

Still yet another feature of the present invention is to provide an apparatus for molding a concrete test cylinder, comprising in combination a concrete test cylinder mold and a cap. The concrete test cylinder mold has a top portion where poured concrete extends therefrom. The cap has at least one radial trough and at least one excretion hole. The cap is manually positioned on the top portion of the concrete test cylinder mold and then pressed and rotated against the top portion of the concrete test cylinder in order to channel excess concrete through the radial trough for excretion through the excretion hole in the cap, thereby creating a uniform concrete test cylinder within the concrete test cylinder mold.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

The invention will become more readily apparent from the following description of preferred embodiments thereof shown, by way of example only, in the accompanying drawings wherein.

Similar reference characters refer to similar parts throughout the several views of the drawings.

DETAILED DESCRIPTION OF THE INVENTION

Figures 1, 2A, 2B:
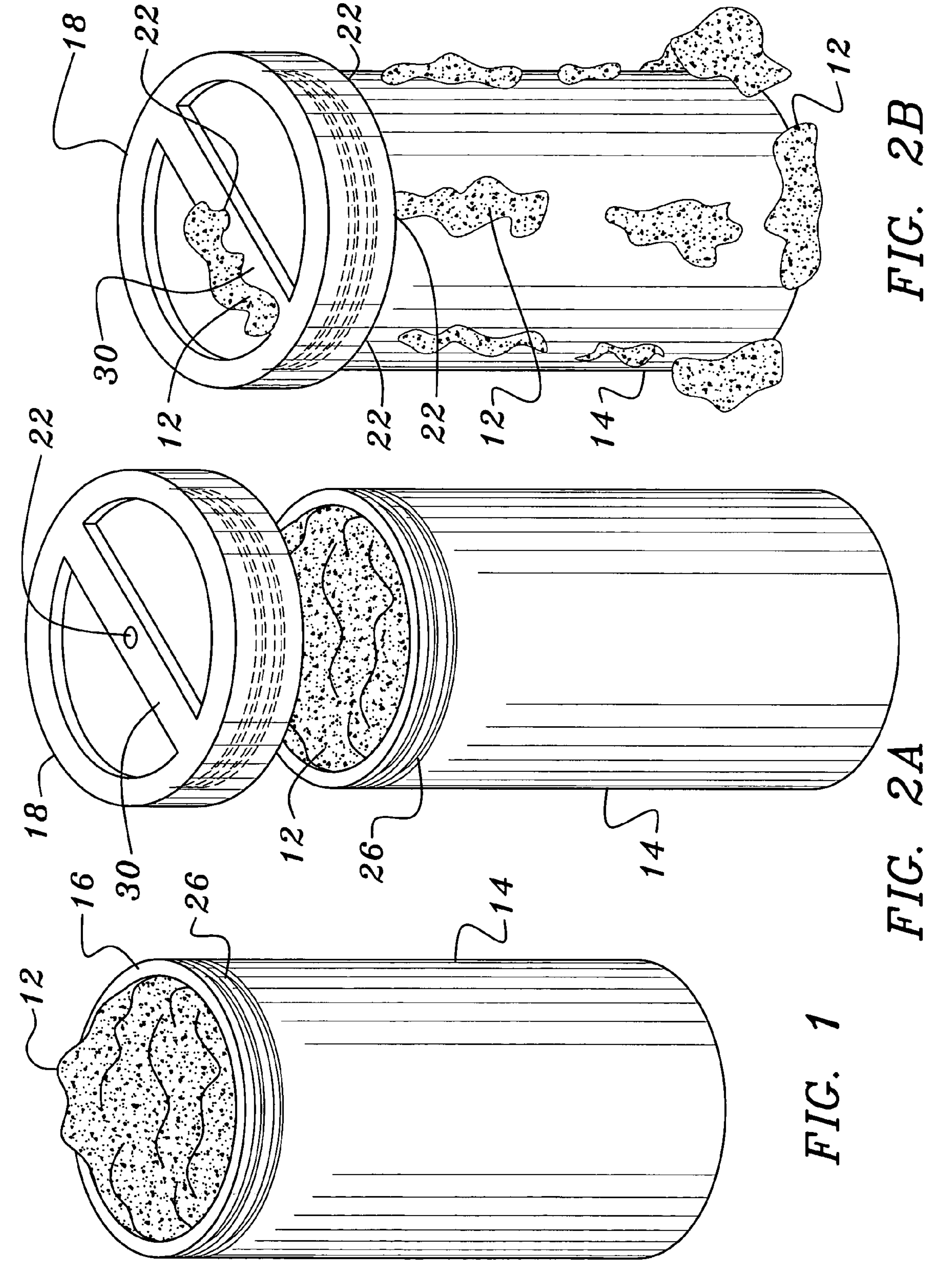
FIG. 1 is a perspective view of a concrete test cylinder mold.
FIG. 2A is a perspective view of a concrete test cylinder mold and a cap before the cap is pressed against the concrete test cylinder mold.
FIG. 2B is a perspective view of a concrete test cylinder mold and a cap after the cap is pressed against the concrete test cylinder mold.

Reference will now be made to the drawings. FIG. 1 shows a standard concrete test cylinder mold 14 filled with concrete 12. The concrete 12 has been added to the concrete test cylinder mold 14 in compliance with the standards set forth by the American Society for Testing Materials (ASTM) for sampling fresh concrete 12.

As shown in FIG. 1 the poured concrete 12 is uneven and extends approximately one quarter of an inch above the top portion 16 of the concrete test cylinder mold 14. In the prior art, the excess concrete 12 that extends above the top portion 16 of the concrete test cylinder mold 14 is manually struck off with a trowel or a float. The prior art method results in varying flatness, height and other non uniformities to the concrete test cylinders that are produced using this prior art method.

Whereas, as best shown in FIG. 2A, the present invention provides a method for making reproducible and uniform concrete test cylinders. As shown in FIG. 1, the fresh concrete 12 is poured into the concrete test cylinder mold 14 pursuant to ASTM regulations. Again, the poured concrete 12 extends above the top portion 16 of the concrete test cylinder mold 14. However, as shown in FIG. 2A a cap 18, built in accordance to one of the embodiments of the present invention 10, is placed on the top portion 16 of the concrete test cylinder mold 14. The cap 18 has at least one excretion hole 22 for allowing excess concrete 12 to be excreted from the concrete test cylinder mold 14.

As best shown in FIG. 2B, in order for the concrete 12 to be excreted, the cap 18 is manually pressed against the top portion 16 of the concrete test cylinder mold 14, whereby excess concrete 12 is excreted through the excretion hole 22 in the top 19 of the cap 18. By pressing on the cap 18, the concrete test cylinder is made level, smooth and uniform within the concrete test cylinder mold 14.

It should be noted that the prior art does provide for a cover for the concrete test cylinder mold, but these covers do not have excretion holes or the ability to smooth or flatten the concrete within the concrete test cylinder mold. Further, due to the inadequacies of the covers of the prior art, most often no cover is placed onto the concrete test cylinder mold.

Figure 3:
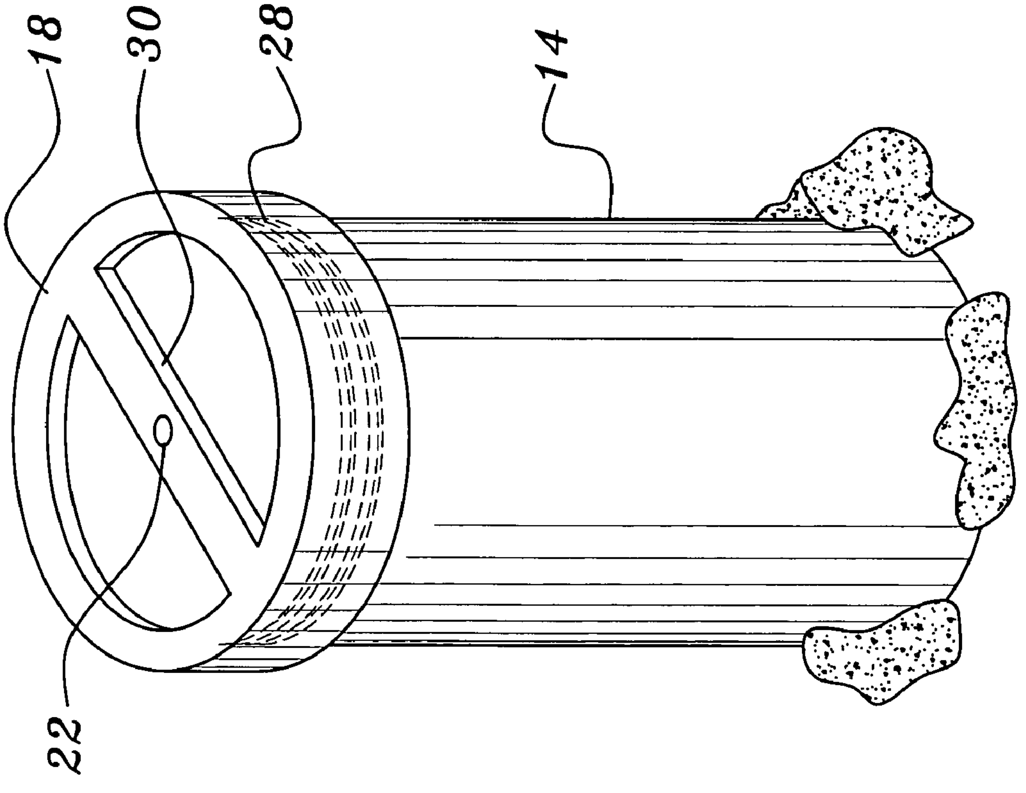
FIG. 3 is a perspective view of a concrete test cylinder mold and a cap after the cap has been rotated against the concrete test cylinder mold.

As best shown in FIG. 3, prior to the initial setting of the concrete 12 within the concrete test cylinder mold 14, the cap 18 is rotated at least a quarter turn to separate the cap 18 from the concrete test cylinder. In another embodiment, the cap 18 can be rotated by turning a handle 30 that is connected to the cap 18. In yet another embodiment, the concrete test cylinder mold 14 can have external screw threads 26 along the top portion 16 as shown in FIG. 1. The cap 18 is internally threaded 28 for threaded engagement with the concrete test cylinder mold as shown in phantom in FIG. 3. After the cap 18 is rotated, the concrete 12 within the concrete test cylinder mold 14 is then cured for a predetermined time according to ASTM standards.

Figure 4:
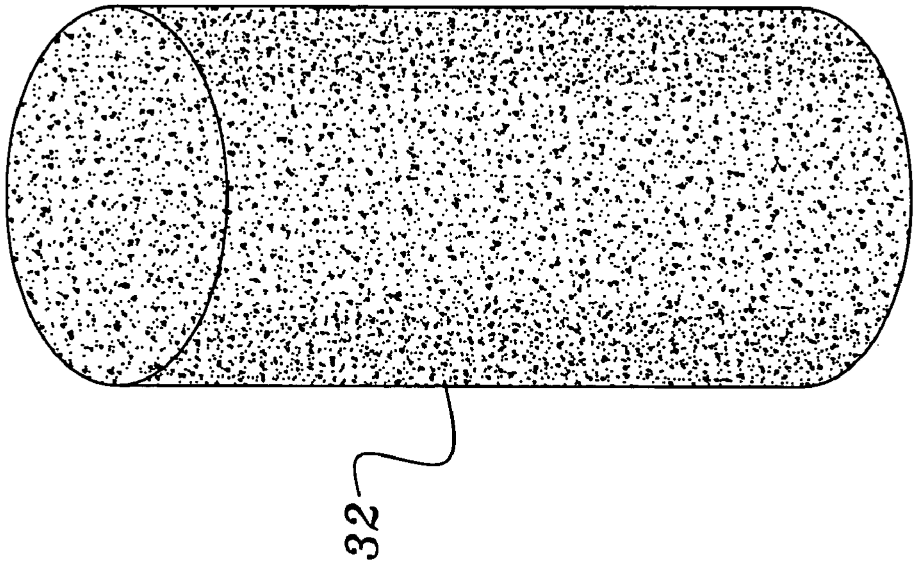
FIG. 4 is a perspective view of a concrete test cylinder produced according to the present invention.

As best shown in FIG. 4, once the concrete is cured, the concrete test sample is removed from the concrete test cylinder mold, whereby a reproducible and uniform concrete test cylinder 32 is produced. Although a cylindrical concrete test cylinder 32 is shown, the concrete test cylinder 32 could be of any closed shape with a variety of cross sections, such as a square, a rectangle, or even a hexagon. Obviously, the shape of the concrete test cylinder 32 produced is dependent on the concrete test cylinder mold used. Further, the present invention can be used on concrete test cylinders molds of varying size as well as rimmed and rimless concrete test cylinder molds. Nevertheless, the present invention will provide the benefits and objects stated regardless of the shape of the mold chosen.

Figure 5:
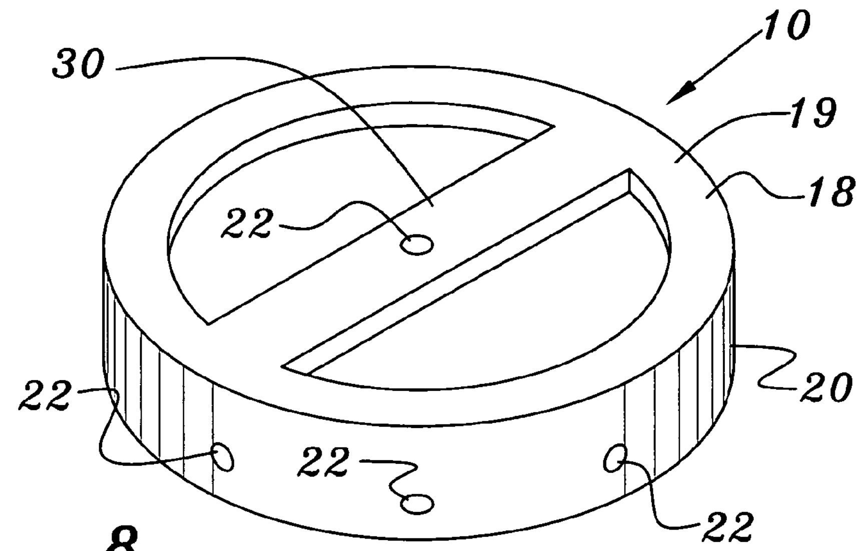
FIG. 5 is a top perspective view of a cap built in accordance with one embodiment of the present invention.

FIG. 5 is a top perspective view of another embodiment of the present invention 10. In this embodiment, the cap 18 has an excretion hole 22 on the top side 19 of the cap 18 and a plurality of excretion holes 22 in the side 20 of the cap 18. In using this cap 18 according to the present invention, the cap is pressed down against the top of a standard concrete test cylinder mold that has been filled with concrete. The pressing action forces excess concrete to be excreted through the excretion holes 22. As a result, a level, smooth and uniform concrete test cylinder is created within the concrete test cylinder mold.

Figure 6:
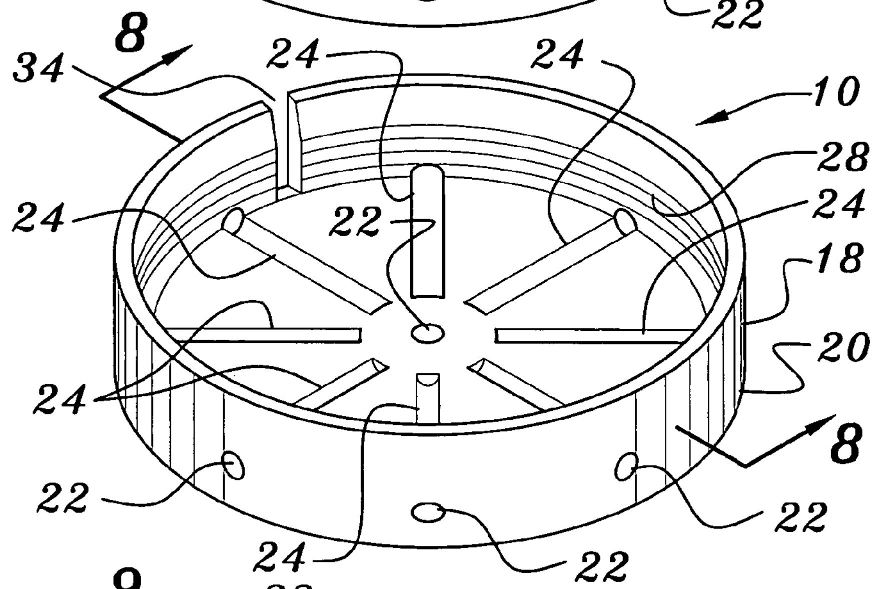
FIG. 6 is a bottom perspective view of a cap built in accordance with one embodiment of the present invention.

The cap 18 shown in FIG. 6 is yet another embodiment of the present invention 10 for a method for making reproducible and uniform concrete test cylinders. The cap 18 of FIG. 6 is used on a standard concrete test cylinder mold that has been filled with fresh concrete pursuant to ASTM regulations. The poured concrete extends above the top portion of the concrete test cylinder mold. The cap 18 has at least one radial trough 24 and at least one excretion hole 22. The cap 18 is placed on the top portion of the concrete test cylinder. The cap 18 is then rotated upon the top of the concrete test cylinder based on the number and dimensions of the radial troughs 24.

In a preferred embodiment, eleven radial troughs having a length of 2¾" and a width of 3⁄32" are positioned within the cap 18. In this preferred embodiment, the cap 18 is rotated approximately one half turn against the top portion of the concrete test cylinder mold. As the cap 18 is rotated, each radial trough 24 channels excess concrete and any air pockets to the excretion holes 22 in the side 20 of the cap 18. In addition, each radial trough 24 smoothes the surface of the concrete within the concrete test cylinder mold. In addition, a tag hole 34 is provided in cap 18 for the purpose of identifying the concrete test sample at the time of testing.

Prior to the initial setting of the concrete within the concrete test cylinder mold the cap 18 is rotated at least a quarter turn to shear the fins created by the troughs and to separate the cap 18 from the concrete test cylinder 32 within the concrete test cylinder mold 14. The cap 18 can be rotated manually or through the use of a handle 30 that is connected to the cap 18. In addition, the cap can be internally threaded 28 for threaded engagement with a concrete test cylinder mold that has been modified with external threads. After the cap 18 is rotated, the concrete within the concrete test cylinder mold is then cured for a predetermined time according to ASTM standards. Then, once the concrete is cured, the concrete test sample is removed from the concrete test cylinder mold, whereby a reproducible and uniform concrete test cylinder is produced.

Figure 7:
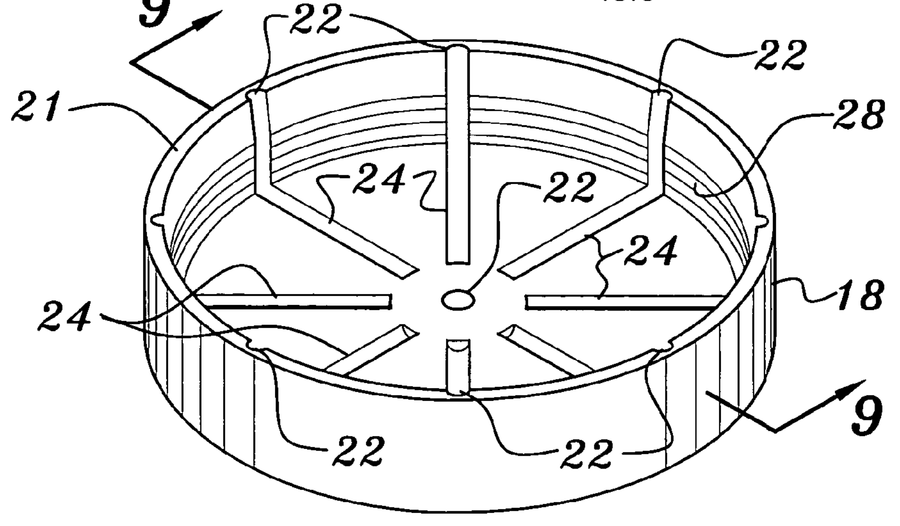
FIG. 7 is a bottom perspective view of a cap built in accordance with one embodiment of the present invention.

The cap 18 shown in FIG. 7 is still yet another embodiment of the present invention 10 for a method for making reproducible and uniform concrete test cylinders. The cap 18 of FIG. 7 is used on a standard concrete test cylinder mold that has been filled with fresh concrete pursuant to ASTM regulations. The poured concrete extends above the top portion of the concrete test cylinder mold. In this embodiment, the cap 18 has at least one radial trough 24 and excretion holes 22 that are positioned in the underside 21 of the cap 18. The cap 18 is placed on the top portion of the concrete test cylinder mold and then the cap 18 is rotated against the top portion of the concrete test cylinder mold. As the cap 18 is rotated, the radial trough 24 channels excess concrete and any air pockets to the excretion holes 22. In addition, the trough 24 smoothes the surface of the concrete within the concrete test cylinder mold.

Prior to the initial setting of the concrete within the concrete test cylinder mold the cap 18 is rotated at least a quarter turn to separate the cap 18 from the concrete test cylinder within the concrete test cylinder mold. The cap 18 can be rotated manually or through the use of a handle 30 that is connected to the cap 18. In addition, the cap can be internally threaded 28 for threaded engagement with a concrete test cylinder mold that has been modified with external threads. After the cap 18 is rotated, the concrete within the concrete test cylinder mold is then cured for a predetermined time according to ASTM standards. Then, once the concrete is cured, the concrete test sample is removed from the concrete test cylinder mold, whereby a reproducible and uniform concrete test cylinder is produced.

Figure 8:
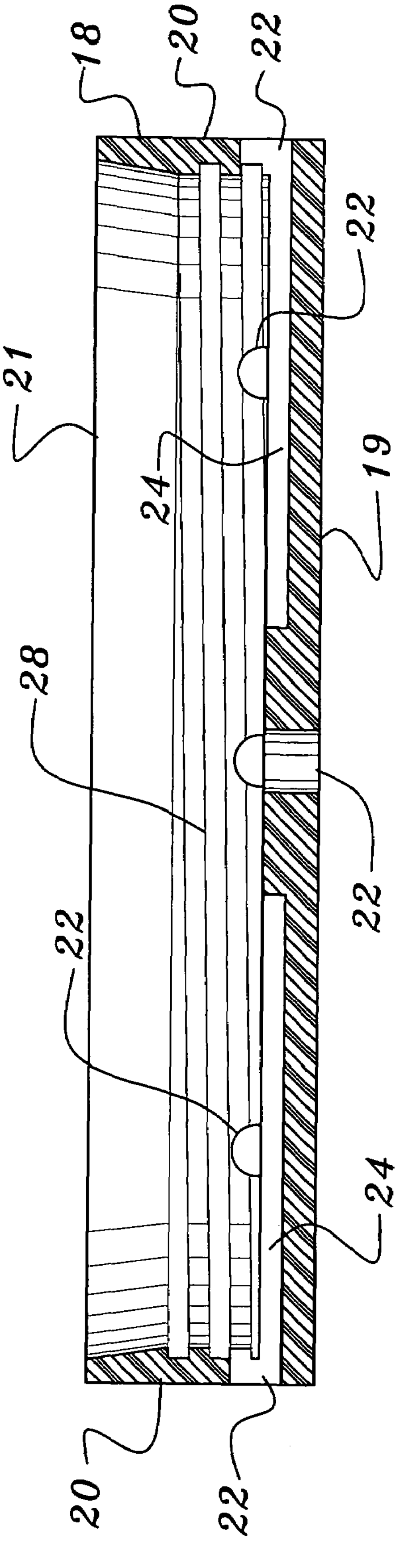
FIG. 8 is a cross sectional view of the cap of FIG. 6 along line 8—8.

FIG. 8 shows a cross sectional view of FIG. 6 along line 8—8. As stated above, in this embodiment, the cap 18 uses radial troughs 24 to channel excess concrete and trapped air to excretion holes 22 that are positioned in the side 20 of the cap 18.

Figure 9:
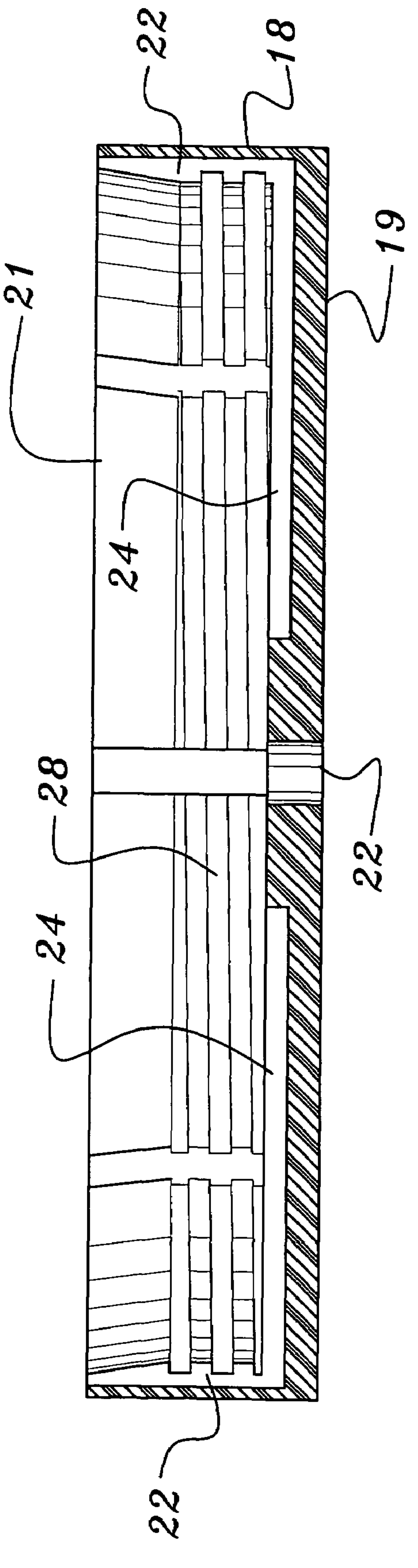
FIG. 9 is a cross sectional view of the cap of FIG. 7 along line 9—9.

FIG. 9 shows a cross sectional view of FIG. 7 along line 9—9. As stated above, in this embodiment, the cap 18 uses radial troughs 24 to channel excess concrete and trapped air to excretion holes 22 that are positioned in the underside 21 of the cap 18.

The cap of the present invention is capable of creating reproducible concrete test cylinders that are flat within one thirty-second of an inch and are perpendicular to the cylinder axis. The concrete test cylinders that are produced using the present invention meet ASTM requirements of being six inches in diameter throughout, twelve inches long and a top and perpendicular to its axis.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

I claim:

1. A method for molding a concrete test cylinder, comprising the steps of:

pouring concrete into a concrete test cylinder mold, said poured concrete extending above a top portion of said concrete test cylinder mold;

placing a cap on said top portion of said concrete test cylinder mold, said cap having at least one excretion hole;

pressing said cap against said top portion of said concrete test cylinder mold, whereby excess concrete is excreted through said excretion hole in said cap;

rotating said cap prior to initial set of said concrete;

curing said poured concrete in said concrete test cylinder mold for a predetermined time; and removing the cured concrete from said concrete test cylinder mold, whereby a reproducible concrete test cylinder is produced.

2. A method for molding a concrete test cylinder, comprising the steps of:

pouring concrete into a concrete test cylinder mold, said poured concrete extending above a top portion of said concrete test cylinder mold;

placing a cap on top of said concrete test cylinder mold, said cap having at least one radial trough and at least one excretion hole;

rotating said cap, whereby excess concrete is channeled by said radial trough for excretion though said excretion hole in said cap;

rotating said cap prior to initial set of said concrete;

curing said poured concrete in said concrete test cylinder mold for a predetermined time; and removing the cured concrete from said concrete test cylinder mold, whereby a reproducible concrete test cylinder is produced.

* * * * *